United States Patent [19]

Holmes

[11] Patent Number: 4,458,877

[45] Date of Patent: Jul. 10, 1984

[54] FLUSHING APPARATUS

[75] Inventor: Martin J. Holmes, Chicago, Ill.

[73] Assignee: The Kendall Company, Boston, Mass.

[21] Appl. No.: 391,205

[22] Filed: Jun. 23, 1982

[51] Int. Cl.³ .......................... F16K 7/06; A61M 5/00
[52] U.S. Cl. ....................................... 251/117; 251/6; 604/250
[58] Field of Search .................... 251/6, 117; 128/675; 604/34, 250

[56] References Cited

U.S. PATENT DOCUMENTS

| | | | |
|---|---|---|---|
| 3,675,891 | 7/1972 | Reynolds et al. | 251/117 |
| 4,187,847 | 2/1980 | Loeser | 604/134 |
| 4,245,636 | 1/1981 | Sparks et al. | 251/117 X |
| 4,335,866 | 6/1982 | Bujan | 251/6 X |
| 4,373,524 | 2/1983 | Leibinsohn | 251/117 X |

Primary Examiner—Dalton L. Truluck

Attorney, Agent, or Firm—Powell L. Sprunger

[57] ABSTRACT

A flushing apparatus comprising, a housing having an inlet, an outlet, a passageway communicating between the inlet and outlet, with the passageway including an insert defining a relatively small bore. The housing has a relatively large bypass channel communicating between the inlet and outlet separately from the passageway, with at least a portion of the channel being defined by a tubular section having flexible walls defining a lumen. The apparatus has a valve member movable between a first closed position with the valve member bearing upon the tubular section such that it blocks the lumen with fluid passing at a relatively slow rate between said inlet and outlet through the bore, and a second open position with the lumen being substantially open such that the fluid passes between said inlet and outlet through the channel at a relatively fast rate.

6 Claims, 8 Drawing Figures

FLUSHING APPARATUS

BACKGROUND OF THE INVENTION

The present invention relates to flushing devices.

During certain medical procedures it is desirable to measure the pressure in the heart. In order to accomplish this result, the distal end of a cardiac catheter is centrally placed in the right side of the heart. It is desirable to prevent blood clots from forming in the catheter, so a heparinized saline solution is slowly passed through the catheter, such as a rate of 3 cubic centimeters per hour. Occasionally, it is desirable to withdraw a blood sample from the catheter. After this has been accomplished, it is desirable to flush the residual blood from the catheter to prevent the catheter from clotting shut. In order to accomplish this result, the catheter is flushed with the saline solution at a relatively fast rate after a blood sample has been taken.

An assortment of devices has been proposed to accomplish flushing, but the devices have been relatively complex, and many require two hands for operation.

SUMMARY OF THE INVENTION

A principal feature of the present invention is the provision of an improved flushing device of simplified construction.

The flushing device of the present invention comprises, a housing having an inlet, an outlet, a passageway communicating between the inlet and outlet, with the passageway including means defining a relatively small bore. The housing has a relatively large bypass channel communicating between the inlet and outlet separately from the passageway, with at least a portion of the channel being defined by a tubular section having flexible walls defining a lumen. The device has valve means movable between a first closed position with the valve means bearing upon the tubular section, and a second open position with the lumen being substantially open.

A feature of the present invention is that the valve means obstructs passage of fluid through the channel in the first position of the valve means, and the fluid passes at a relatively low rate through the bore.

Another feature of the invention is that when the valve means is at the second position the device permits a fast flow or flushing of fluid through the channel between the inlet and outlet.

Still another feature of the invention is the provision of means for indicating when the valve means is located at the second position.

Yet another feature of the invention is that the valve means may be moved to a variable intermediate position with the tubular section partially closed.

Further features will become more fully apparent in the following description of the embodiments of this invention and from the appended claims.

DESCRIPTION OF THE PREFERRED EMBODIMENTS

Figure 1:
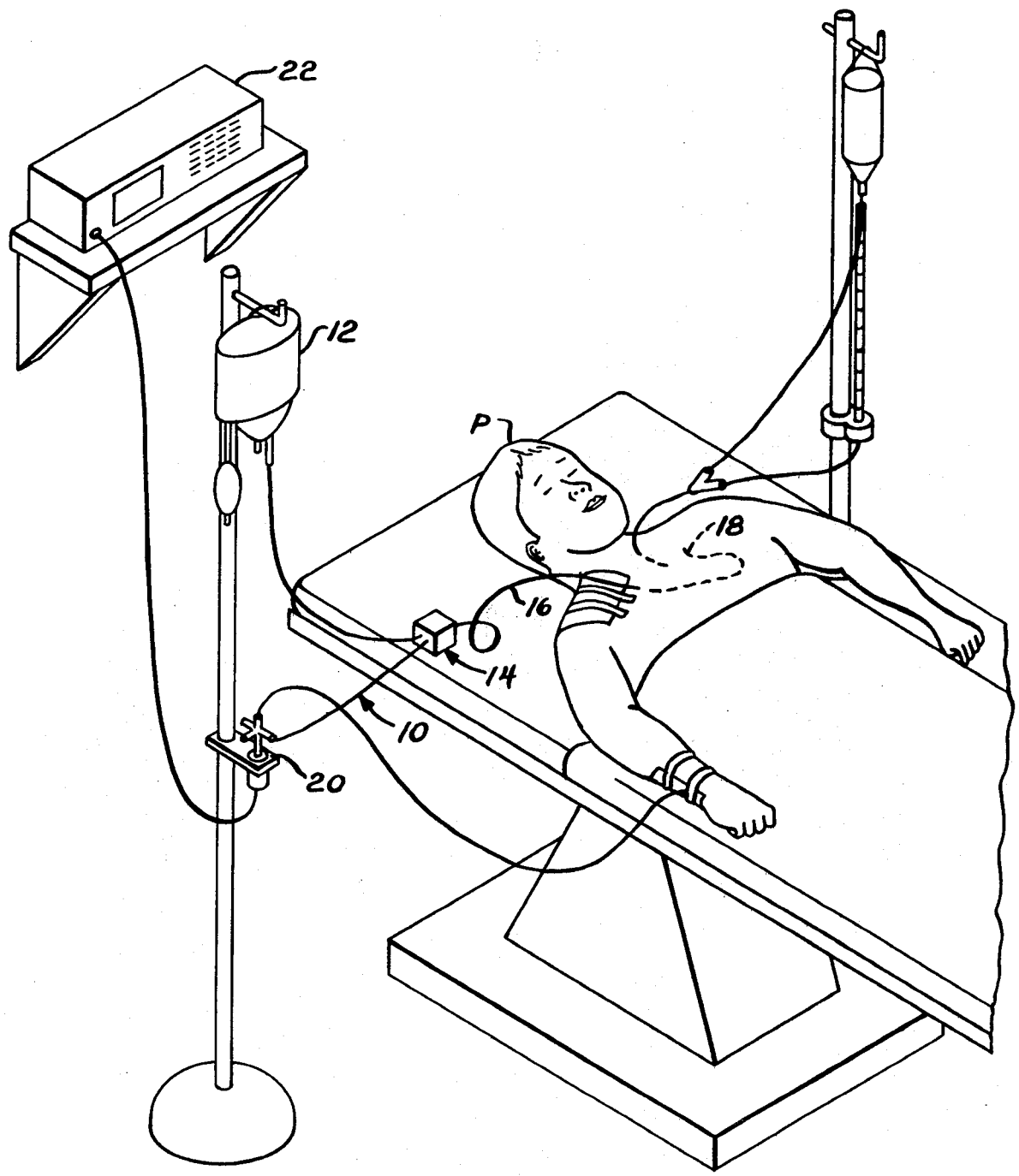
FIG. 1 is a perspective view of an intravenous system including a flushing device of the present invention for a patient.
Figure 2:
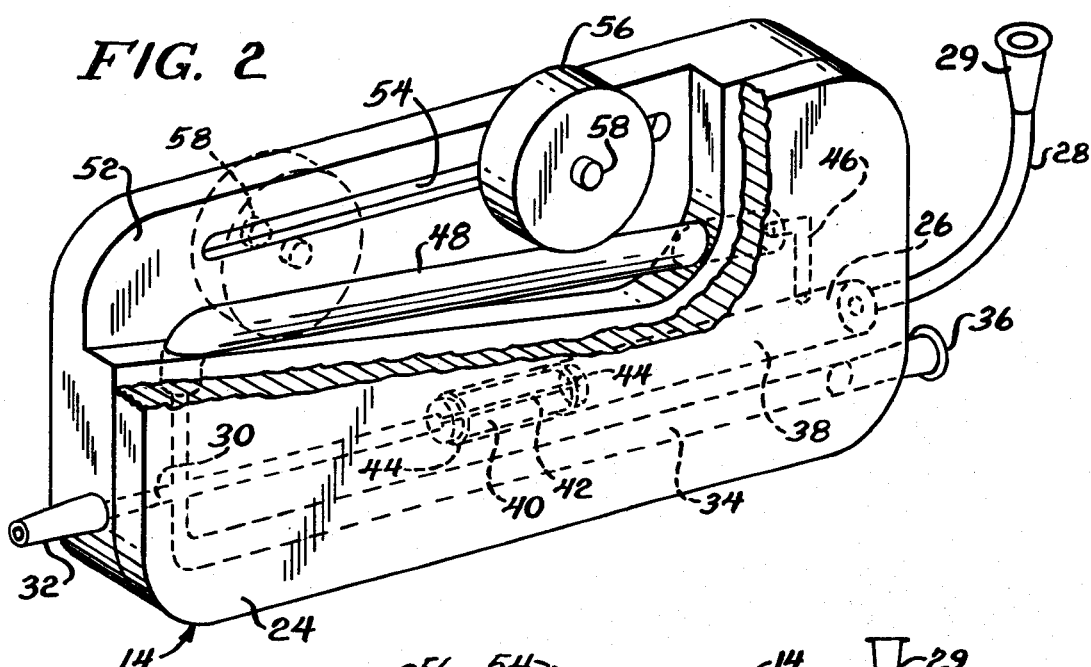
FIG. 2 is a fragmentary perspective view of the flushing device of the present invention.
Figure 3:
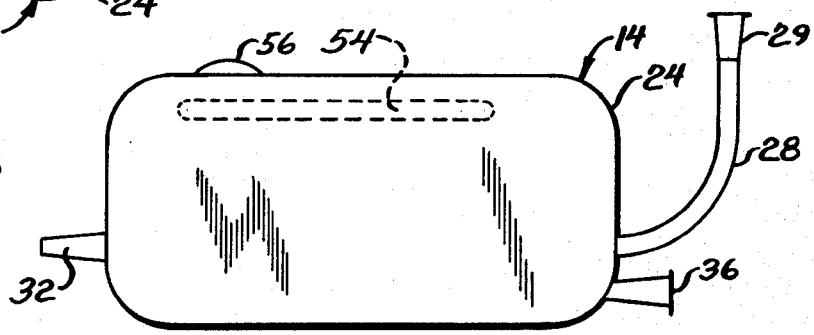
FIG. 3 is an elevational view of the flushing device of FIG. 2.

Referring now to FIG. 1, there is shown an intravenous system generally designated 10 comprising a source 12 of intravenous fluid, such as heparinized saline solution, which is connected to a flushing device 14 which normally permits a relatively slow flow of the saline solution through the device 14, such as 3 cubic centimeters per hour, into a cardiac catheter 16 which is connected to the flushing device 14 and has a distal end 18 centrally placed in the right side of the heart of a patient P. The flushing device 14 is connected to a pressure transducer 20 which in turn is connected to suitable electronic equipment 22 to indicate the pressure in the patient's heart.

A flushing device 14 of the present invention is illustrated in FIGS. 2–5. The flushing device 14 has a housing 24 which may be constructed of a suitable plastic material. The housing 24 has an inlet 26 communicating with a tube 28 having a hub 29 which is connectable to the source 12 of liquid. The housing 24 has an outlet 30 which communicates through a hollow nipple 32 with the cardiac catheter 16 leading to the patient. The housing 24 has a channel 34 communicating between the outlet 30 and a hub 36 which is connectable to the pressure transducer 20.

The housing 24 has an elongated passageway 38 communicating between the inlet 26 and outlet 30. As shown, the housing 24 has an insert 40 received in the passageway 38, with the insert 40 having a relatively small bore 42 extending therethrough, such as 0.002 to 0.003 inches in diameter. The insert 40 has a pair of spaced O-rings 44 extending around the insert 40 and engaging against an inner surface of the passageway 38 to prevent passage of liquid around the insert 40. As will be discussed further below, liquid normally passes through the insert bore 42 at a relatively slow rate, such as 3 cubic centimeters per hour.

The housing 24 has a relatively large bypass channel 46 communicating between the inlet 26 and outlet 30 separately from the passageway 38. At least a portion of the channel 46 is defined by an elongated tubular section 48 having flexible walls, such as a suitable plastic material, e.g., polyvinylchloride, with the tubular section 48 defining a lumen 50. As shown, at least a central portion of the tubular section 48 is substantially straight.

The housing 24 has a cutout 52 in the region of the tubular section 48, with the housing 24 having a pair of opposed generally straight grooves 54 disposed at a slight angle relative to the central portion of the tubular section 48. The device 14 has a generally cylindrical valve element 56 which may be made of a suitable plastic material. The valve element 56 has a pair of opposed centrally located pins 58 slidably received in the grooves 54.

Figure 4:
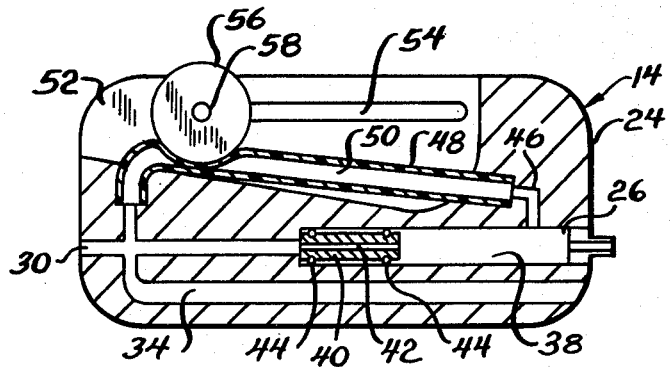
FIG. 4 is a sectional view of the flushing device with a valve element in a first closed position.
Figure 5:
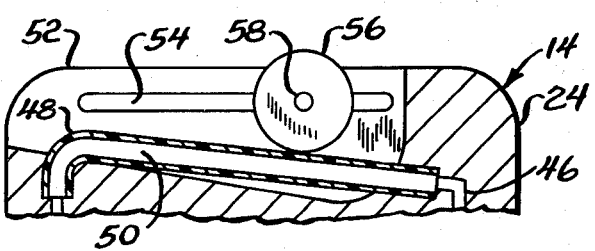
FIG. 5 is a fragmentary sectional view of the flushing device with the valve element at a second open position.

With reference to FIG. 4, the valve element 56 is movable between a first closed position, and, with reference to FIG. 5, a second open position. With reference to FIG. 4, when the valve element 56 is located at the first position, the valve element 56 bears upon the walls of the tubular section 48 and closes the lumen 50. In this configuration, the liquid passes from the inlet 26 through the insert bore 42 at a relatively slow rate to the outlet 30. With reference to FIG. 5, when the valve element 56 is located at the second open position, the valve element 56 slightly contacts the tubular section 48 or is spaced from the tubular section 48. In this configuration, the lumen 50 of the tubular section 48 is substantially open, and liquid passes at a relatively fast rate through the channel 46 between the inlet 26 and outlet 30 in order to flush the catheter 16. Of course, with reference to FIGS. 4 and 5, the valve element 56 may be located at variable intermediate positions between the first and second positions with the valve element 56 only partially occluding the lumen 50 in order to permit a variable selection of a slower passage of liquid through the lumen 50 relative to the amount of liquid passing through the lumen 50 at the second position of the valve element 56.

In use, the flushing device 14 is connected in the system 10, and as shown in FIG. 4 the valve element 56 is moved to the first closed position in order to block passage of liquid through the channel 46, and cause relatively slow passage of liquid through the insert bore 42. When it is desired to flush the catheter 16, the valve element 56 is moved to the second open position, as shown in FIG. 5, or to an intermediate position in order to permit a relatively fast flow of liquid through the channel 46. After flushing has been completed, the valve element 56 is again moved to the first closed position, as shown in FIG. 4, in order to block the channel 46. The flushing device 14 of the present invention permits manipulation of the valve element 56 between the first and second positions with the use of one hand in order to facilitate operation of the device 14.

Figure 6:
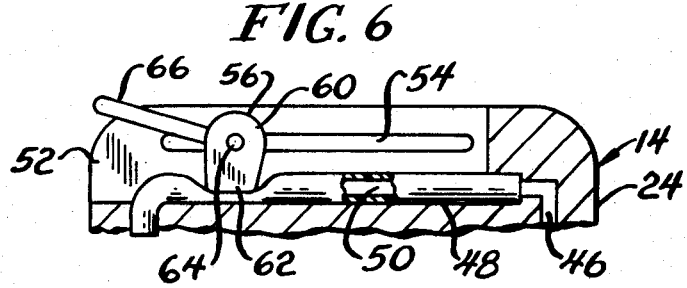
FIG. 6 is a fragmentary sectional view of another embodiment of the flushing device showing a cam in a first closed position.
Figure 7:
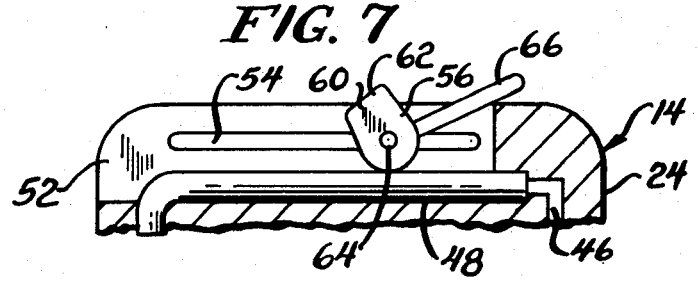
FIG. 7 is a fragmentary sectional view showing the cam in a second open position.

Another embodiment of the present invention is illustrated in FIGS. 6 and 7, in which like reference numerals designate like parts. In this embodiment, the grooves 54 are substantially aligned with the central portion of the tubular section 48. The valve element 56 comprises a cam 60 having an enlarged lobe 62, and a pair of opposed pins 64 slidably received in the grooves 54. Also, the valve element 56 has a handle 66 connected to the cam 60.

In this embodiment, the handle 66 is movable between a first closed position, as shown in FIG. 6, with the lobe 62 of the cam 60 bearing against the tubular section 48 and closing the lumen 50 in order to obstruct passage of liquid through the channel 46. With reference to FIG. 7, the handle 66 is movable to a second open position with the cam lobe 62 spaced from the tubular section 48 in order to open the lumen 50, and permit the fast flow of liquid through the channel 46. In other respects, the flushing device 14 of FIGS. 6 and 7 operates in substantially the same manner as the flushing device 14 of FIGS. 2-5.

Figure 8:
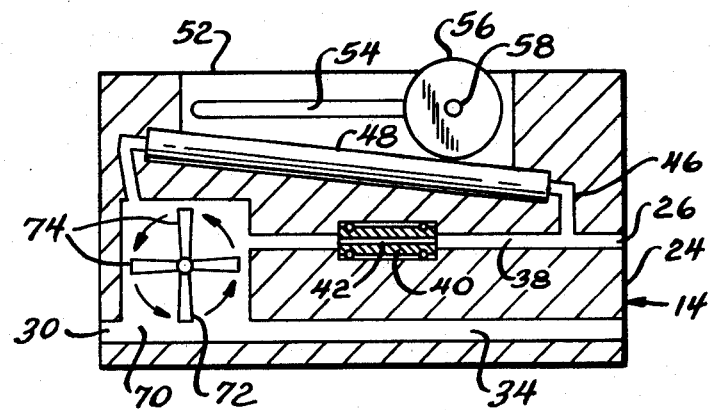
FIG. 8 is a sectional view of another embodiment of the present invention.

Another embodiment of the present invention is illustrated in FIG. 8, in which like reference numerals designate like parts. In this embodiment, the housing 24 has a cavity 70 communicating between the channel 46 and outlet 30. The device 14 has a paddle wheel 72 having a plurality of blades 74 pivotally mounted in the cavity 70, such that outer ends of the blades 74 are located adjacent the channel 46. In this embodiment, the housing 24 is transparent, such that the paddle wheel 72 is visible from the outside of the housing 24.

In use, the paddle wheel 72 does not rotate or rotates at a relatively slow rate when the channel 46 is blocked by the valve element 56 and the liquid is passing at a relatively slow rate through the insert bore 42. However, when the valve element 56 is moved to the second open position, the liquid passing at a fast rate through the channel 46 strikes against the outer ends of the blades 74, and rotates the paddle wheel 72 at a fast rate which is visible outside the housing 24. Thus, the paddle wheel 72 provides an indication when the channel 46 is open, and when the liquid is passing at a relatively fast rate between the inlet 26 and outlet 30.

The foregoing detailed description is given for clearness of understanding only, and no unnecessary limitations should be understood therefrom, as modifications will be obvious to those skilled in the art.

I claim:

1. A flushing device, comprising:
   a housing having an inlet, an outlet, a passageway communicating between the inlet and outlet, said passageway including means defining a relatively small bore, and a relatively large bypass channel communicating between said inlet and outlet separately from said passageway, with at least a portion of said channel being defined by a tubular section having flexible walls defining a lumen; and
   valve means movable between a first closed position with the valve means bearing upon and restricting the tubular section such that opposed walls of the tubular section engage each other and such that it blocks the lumen with fluid passing at a relatively slow rate between said inlet and outlet through said bore, and a second open position with said lumen being substantially open such that said fluid passes between said inlet and outlet through said channel at a relatively fast rate.

2. The device of claim 1 wherein said valve means is movable to at least one intermediate position with said lumen partially closed.

3. The device of claim 1 wherein said tubular section is substantially straight, and in which said housing includes a pair of opposed substantially straight grooves located at a slight angle relative to the tubular section, and including a cylindrical valve element having a pair of opposed centrally located pins slidably received in said grooves, said valve element being movable between a first position in said groove with the valve element bearing upon said tubular section and closing the lumen, and a second position in said grooves with the lumen substantially open.

4. The device of claim 3 wherein the valve element is spaced from the tubular section at said second position.

5. The device of claim 1 wherein the valve means comprises a cam having a lobe, said cam being movable between a first position with the lobe compressing the tubular section and closing the lumen, and a second position with the lumen substantially open.

6. The device of claim 5 wherein the lobe is spaced from the tubular section at said second position.

* * * * *